United States Patent [19]

Karrer et al.

[11] 3,957,885

[45] May 18, 1976

[54] ETHER DERIVATIVES OF DIPHENYLMETHANES

[75] Inventors: Friedrich Karrer, Basel; Saleem Farooq, Aesch, both of Switzerland

[73] Assignee: Ciba-Geigy Corporation, Ardsley, N.Y.

[22] Filed: Apr. 23, 1975

[21] Appl. No.: 570,978

[30] Foreign Application Priority Data
Apr. 26, 1974  Switzerland.......................... 5756/74
Mar. 14, 1975  Switzerland.......................... 3260/75

[52] U.S. Cl............................. 260/613 R; 260/591; 260/609 E; 260/609 F; 424/331; 424/337; 424/341
[51] Int. Cl.².......................................... C07C 43/20
[58] Field of Search ................................ 260/613 R

[56] References Cited
UNITED STATES PATENTS
2,331,090  10/1943  Gabel et al.................. 260/613 R X
3,131,166  4/1964  Harris et al. ................ 260/613 R X FOREIGN PATENTS OR APPLICATIONS
44-1531  1/1969  Japan.............................. 260/613 R

*Primary Examiner*—Bernard Helfin
*Attorney, Agent, or Firm*—Fredrick H. Rabin; Harry Falber

[57] ABSTRACT

New 1-phenoxy- or 1-phenylthio-, 2-alkyl-, 2-alkenyl-, 2-alkynyl-oxy or -thio ethane derivatives, their manufacture and use for the control of insects and representatives of the order acarina are disclosed. The compounds correspond to the formula

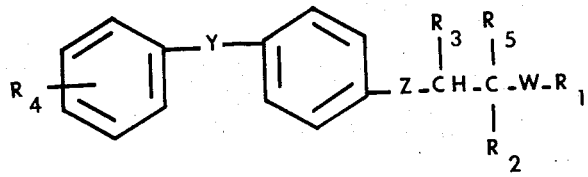

wherein
  W and Z each represent —O— or —S—,
  Y represents —CH$_2$—, —CO— or —S—,
  R$_1$ represents C$_1$–C$_6$-alkyl, C$_2$–C$_4$-alkenyl, C$_2$–C$_4$-haloalkenyl, C$_3$–C$_4$-alkynyl, C$_3$–C$_6$-cycloalkyl or benzyl,
  R$_2$ represents hydrogen, methyl or ethyl,
  R$_3$ represents hydrogen or methyl, or
  R$_2$ and R$_3$ together with the chain represent a saturated 5- or 6-membered ring, and
  R$_4$ represents hydrogen, methyl or halogen, and
  R$_5$ represents hydrogen or methyl.

5 Claims, No Drawings

ETHER DERIVATIVES OF DIPHENYLMETHANES

The present invention relates to compounds of the formula

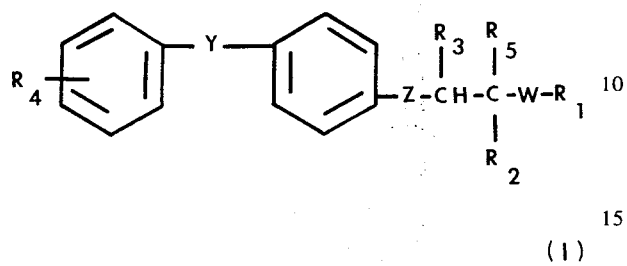

(I)

wherein
W and Z each represent —O— or —S—,
Y represents —CH$_2$—, —CO— or —S—,
R$_1$ represents C$_1$–C$_6$-alkyl, C$_2$–C$_4$-alkenyl, C$_2$–C$_4$-haloalkenyl, C$_3$–C$_4$-alkynyl, C$_3$–C$_6$-cycloalkyl or benzyl,
R$_2$ repesents hydrogen, methyl or ethyl,
R$_3$ represents hydrogen or methyl, or
R$_2$ and R$_3$ together with the chain represent a saturated 5- or 6-membered ring, and
R$_4$ represents hydrogen, methyl or halogen, and
R$_5$ represents hydrogen or methyl,
and to processes for their production and to their use in pest control.

The alkyl, alkenyl or alkynyl chains denoted by R$_1$ can be straight-chain or branched-chain. Examples are, inter alia: methyl, ethyl, isopropyl, n-propyl, n-, i-, sec.-, tert.-butyl, n-pentyl, n-hexyl and isomers thereof, allyl, methallyl or propargyl.

Compounds of formula I particularly preferred on account of their action are those wherein
W and Z each represent —O— or —S—,
Y represents —CH$_2$— or —S—,
R$_1$ represents C$_1$–C$_6$-alkyl, C$_2$–C$_4$-alkenyl, C$_3$–C$_4$—Cl-alkenyl or C$_3$–C$_4$-alkenyl,
R$_2$ represents hydrogen or methyl,
R$_3$ and R$_5$ represent hydrogen, and
R$_4$ represents bromine.

More especially preferred, however, are compounds of formula I wherein
W and Z each represent —O—,
Y represents —CH$_2$— or —S—,
R$_1$ represents methyl, ethyl, isopropyl, isobutyl, sec.-butyl, allyl or propargyl, and
R$_2$ represents hydrogen or methyl, and
R$_3$, R$_4$ and R$_5$ each represent hydrogen.

The compounds of formula I can be produced by, for example, the following methods known per se:

1) 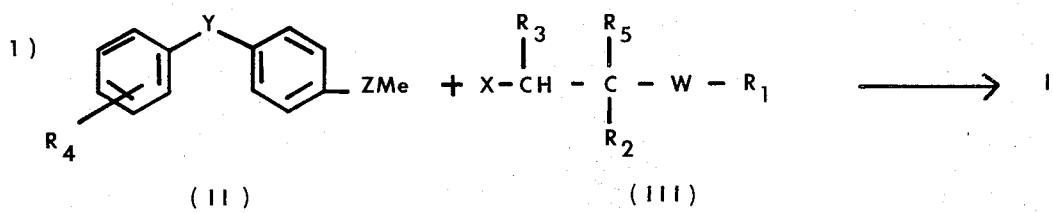

2) 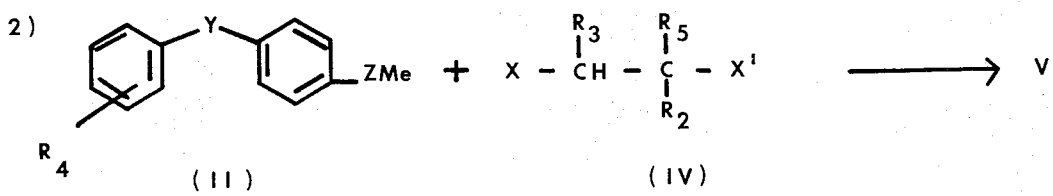

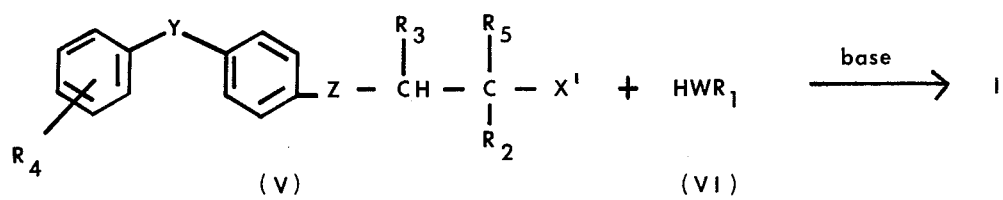

3)
a)
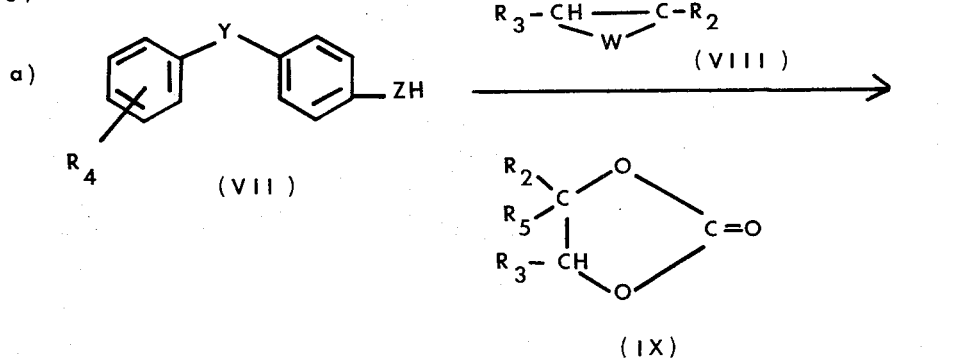
b)
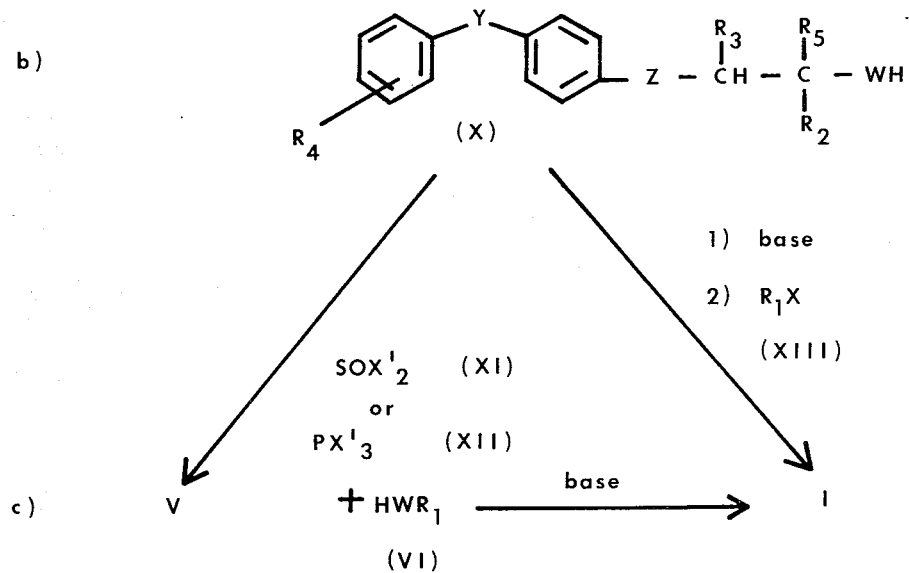
c)
4)
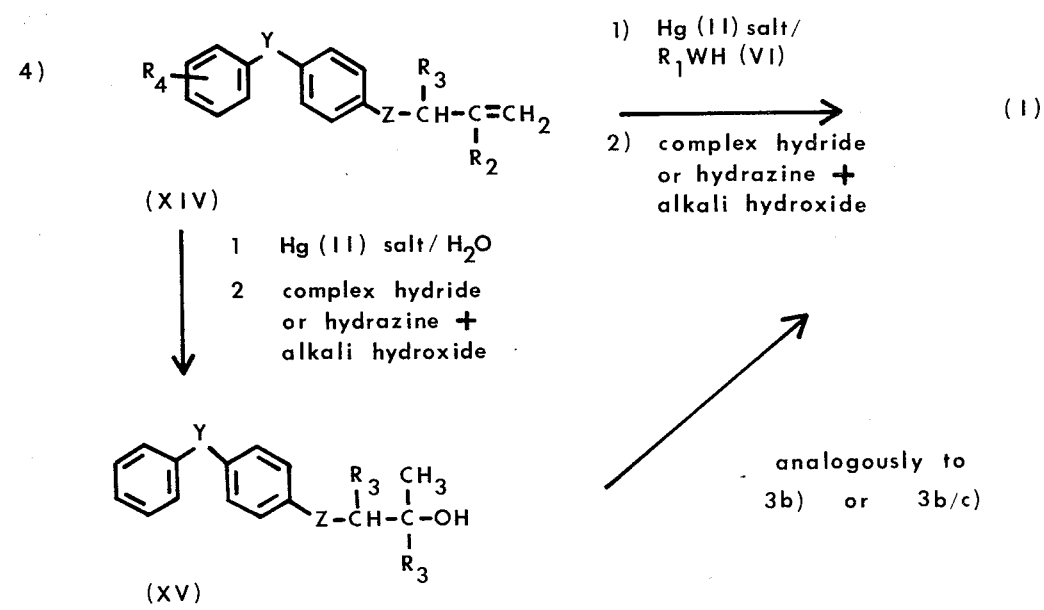

In formulae II to XV, the symbols $R_1$ to $R_5$, W, Y and Z have the meanings given for formula I, X stands for halogen, X' stands for halogen, $CH_3-SO_2-$ or

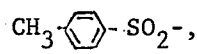

and Me stands for a metal of the first or second main group of the periodic system.

The compounds of formula I are suitable for the control of various animal and plant pests. They are particularly suitable for the control of insects of the families: Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineididae, Noctuidae, Lymantriidae, Pyralidae, Galleridae, Culicidae, Tipulidae, Stomoxydae, Muscidae, Calliphoridae, Trypetidae and Pulicidae, as well as acarids of the Tetranychidae family.

The insecticidal and acaricidal action can be appreciably broadened and adapted to suit given conditions by the addition of other insecticides and/or acaricides. Suitable additives are, e.g., organic phosphorus compounds, nitrophenols and derivatives thereof, formamidines, ureas, carbamates or chlorinated hydrocarbons and pyrethroids.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents that are inert to the active substances. The active substances can be obtained and used in the following forms:

Solid Preparations dusts, scattering agents, granulates, coated granulates, impregnated granulates and homogeneous granulates;

Liquid Preparations a. water-dispersible active-substance concentrates: wettable powders, pastes or emulsions,
b. solutions.

The content of active substance in the described preparations is between 0.1 and 95%.

The active substances of formula I can be formulated, for example, as follows:

Dusts

The following substances are used to prepare (a) a 5% dust, and (b) a 2% dust:
a.
  5 parts of active substance,
  95 parts of talcum;
b.
  2 parts of active substance,
  1 part of highly dispersed silicic acid,
  97 parts of talcum.

The active substances are mixed and ground with the carriers.

Granulate

The following substances are used to produce a 5% granulate:
  5 parts of active substance,
  0.25 part of epichlorohydrin,
  0.25 part of cetyl polyglycol ether,
  3.50 parts of polyethylene glycol,
  91 parts of kaolin (particle size 0.3 – 0.8 mm).

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder

The following constituents are used in the preparation of (a) a 40%, (b) and (c) a 25%, and (d) a 10% wettable powder:
a.
  40 parts of active substance,
  5 parts of sodium lignin sulphonate,
  1 part of sodium dibutyl-naphthalene sulphonate,
  54 parts of silicic acid;
b.
  25 parts of active substance,
  4.5 parts of calcium lignin sulphonate,
  1.9 parts of Champagne chalk/hydroxyethyl cellulose mixture (1:1),
  1.5 parts of sodium dibutyl naphthalene sulphonate,
  19.5 parts of silicic acid
  19.5 parts of Champagne chalk,
  28.1 parts of kaolin;
c.
  25 parts of active substance,
  2.5 parts of isooctylphenoxy-polyoxyethyleneethanol,
  1.7 parts of Champagne chalk/hydroxyethyl cellulose mixture (1:1),
  8.3 parts of sodium aluminum silicate,
  16.5 parts of kieselgur,
  46 parts of kaolin;
d.
  10 parts of active substance,
  3 parts of a mixture of the sodium salts of saturated fatty alcohol sulphates,
  5 parts of naphthalenesulphonic acid/formaldehyde condensate,
  82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable Concentrates

The following substances are used to produce (a) a 10%, (b) a 25% and (c) a 50% emulsifiable concentrate:
a.
  10 parts of active substance,
  3.4 parts of epoxidised vegetable oil,
  3.4 parts of a combination emulsifier consisting of fatty alcohol polyglycol ether and alkylarylsulphonate calcium salt, 40 parts of dimethylformamide,
43.2 parts of xylene;
b.
25 parts of active substance,
2.5 parts of epoxidised vegetable oil,
10 parts of alkylarylsulphonate/fatty alcohol-polyglycol ether mixture,
5 parts of dimethylformamide,
57.5 parts of xylene;
c.
50 parts of active substance,
4.2 parts of tributylphenol-polyglycol ether,
5.8 parts of calcium-dodecylbenzenesulphate,
20 parts of cyclohexanone,
20 parts of xylene.

It is possible to prepare from these concentrates, by dilution with water, emulsions of any desired concentration.

Spray

The following constituents are used to produce (a) a 5% spray and (b) a 95% spray:
a.
5 parts of active substance,
1 part of epichlorohydrin,
94 parts of ligroin (boiling limits 160°–190°C);
b.
95 parts of active substance,
5 parts of epichlorohydrin.

EXAMPLE 1

28.2 g of 2-chloroethyl-ethyl ether is added dropwise in the course of one hour at a bath temperature of 105°–110°C, with stirring, to a mixture of 36.8 g of 4-benzylphenol, 40 g of finely pulverised anhydrous potassium carbonate, 0.5 g of potassium iodide, 0.1 g of hydroquinone, 90 ml of hexamethylphosphoric acid triamide and 90 ml of dimethylformamide; and the mixture is held for a further 20 hours at this temperature. In further processing, the cooled reaction mixture is poured into about 800 ml of ice water, and extraction is repeatedly performed with ether. The combined ether phases are washed neutral with 10% potassium hydroxide solution followed by saturated sodium chloride solution; they are then dried over sodium sulphate and treated with active charcoal. After the solvent has been distilled off, the crude product is chromatographed on silica gel (eluant: diethyl ether/hexane 1:4) to yield pure 1-benzyl-4-(2-ethoxy)-ethoxybenzene ($n_D^{20}$: 1.5502).

The following compounds can be produced in an analogous manner:

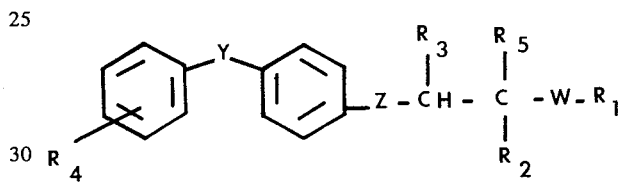

| | | $R_4 = H$ | | | | | |
|---|---|---|---|---|---|---|---|
| $R_1$ | $R_2$ | $R_3$ | $R_5$ | W | Y | Z | Physical data |
| —CH$_2$—C≡CH | H | H | H | —O— | —CH$_2$— | —O— | |
| —O—3H$_7$ | H | H | H | —O— | —CH$_2$— | —O— | $n_D^{20}$ 1,5447 |
| —C$_4$H$_9$ | H | H | H | —O— | —CH$_2$— | —O— | $n_D^{20}$ 1,5391 |
| —C$_3$H$_7$ (i) | H | H | H | —O— | —CH$_2$— | —O— | $n_D^{20}$ 1,5410 |
| —CH$_2$—CH=CH$_2$ | H | H | H | —O— | —CH$_2$— | —O— | |
| —CH$_2$—CH=CH—Cl | H | H | H | —O— | —CH$_2$— | —O— | |
| —CH=CH$_2$ | H | H | H | —O— | —CH$_2$— | —O— | |
| —CH$_2$—C≡CH | —CH$_3$ | H | H | —O— | —CH$_2$— | —O— | |
| —CH$_2$—C≡CH | H | —CH$_3$ | H | —O— | —CH$_2$— | —O— | |
| —CH$_2$—C≡CH | —CH$_2$—CH$_2$—CH$_2$— | | H | —O— | —CH$_2$— | —O— | |
| —C$_2$H$_5$ | —⌬ | H | H | —O— | —CH$_2$— | —O— | |
| —CH$_2$—C≡CH | —⌬ | H | H | —O— | —CH$_2$— | —O— | |
| —C$_2$H$_5$ | —CH$_3$ | H | —CH$_3$ | —O— | —CH$_2$— | —O— | $n_D^{20}$ 1,5422 |
| —CH$_3$ | H | H | H | —O— | —CH$_2$— | —O— | $n_D^{20}$ 1,5596 |
| —C$_2$H$_5$ | —CH$_3$ | H | H | —O— | —CH$_2$— | —O— | |
| —C$_4$H$_{9(i)}$ | —CH$_3$ | H | H | —O— | —CH$_2$— | —O— | |
| —C$_2$H$_5$ | H | —CH$_3$ | H | —O— | —CH$_2$— | —O— | |
| —CH$_2$—C≡CH | H | —CH$_3$ | H | —O— | —CH$_2$— | —O— | |
| —C$_2$H$_5$ | —CH$_3$ | —CH$_3$ | H | —O— | —CH$_2$— | —O— | |
| —CH$_2$—C≡CH | —CH$_3$ | —CH$_3$ | H | —O— | —CH$_2$— | —O— | |
| —C$_2$H$_5$ | —CH$_2$—CH$_2$—CH$_2$—CH$_2$— | | H | —O— | —CH$_2$— | —O— | |
| —CH$_2$—C≡CH | —CH$_2$—CH$_2$—CH$_2$—CH$_2$— | | H | —O— | —CH$_2$— | —O— | |
| —CH$_2$—C≡CH | H | H | H | —O— | —CH$_2$— | —S— | |
| —C$_2$H$_5$ | H | H | H | —O— | —CH$_2$— | —S— | |
| —C$_3$H$_{7(i)}$ | H | H | H | —S— | —CH$_2$— | —O— | |
| —C$_2$H$_5$ | H | H | H | —S— | —CH$_2$— | —O— | |
| —CH$_3$ | H | H | H | —S— | —CH$_2$— | —O— | $n_D^{20}$ 1,5862 |
| —C$_2$H$_5$ | H | H | H | —O— | —C(=O)— | —O— | $n_D^{20}$ 1,5832 |
| —CH$_2$—C≡CH | H | H | H | —O— | —C(=O)— | —O— | |
| —CH—C≡CH<br>  \|<br>  CH$_3$ | H | H | H | —O— | —C(=O)— | —O— | |
| —C$_4$H$_{9(i)}$ | H | H | H | —O— | —C(=O)— | —O— | |
| —C$_2$H$_5$ | —CH$_3$ | H | H | —O— | —C(=O)— | —O— | |

-continued

| $R_1$ | $R_2$ | $R_3$ | $R_4 = H$ $R_5$ | W | Y | Z | Physical data |
|---|---|---|---|---|---|---|---|
| —CH₂—C≡CH | H | H | H | —O— | —S— | —O— | $n_D^{20}$ 1,6025 |
| —CH₂—C≡CH | —CH₃ | —CH₃ | H | —O— | —C(=O)— | —O— | |
| —C₂H₅ | —CH₃ | —CH₃ | H | —O— | —C(=O)— | —O— | |
| —C₂H₅ | —C₆H₅ | H | H | —O— | —C(=O)— | —O— | |
| —CH₃ | —C₆H₅ | H | H | —O— | —C(=O)— | —O— | |
| —CH₂—C≡CH | —CH₃ | H | H | —O— | —S— | —O— | $n_D^{20}$ 1,5889 |
| —C₂H₅ | H | —CH₃ | H | —O— | —C(=O)— | —O— | |
| —C₃H₇ | H | H | H | —O— | —S— | —O— | $n_D^{20}$ 1,5983 |
| —CH₂—CH=CHCl | H | H | H | —O— | —S— | —O— | $n_D^{20}$ 1,6042 |
| —C₂H₅ | H | H | H | —O— | —S— | —O— | $n_D^{20}$ 1,5906 |
| —CH₂—C≡CH | H | H | H | —O— | —S— | —S— | |
| —CH₂—CH=CH—CH₃ | H | H | H | —O— | —S— | —O— | $n_D^{20}$ 1,5875 |
| —C₂H₅ | H | H | H | —O— | —S— | —O— | |
| —C₃H₇ | H | H | H | —O— | —O— | —O— | |
| —CH₃ | H | H | H | —S— | —S— | —O— | $n_D^{20}$ 1,6269 |
| i-C₃H₇ | H | H | H | —O— | —S— | —O— | $n_D^{20}$ 1,5718 |
| —CH₂—C≡CH | H | H | H | —O— | —C(=O)— | —O— | |
| —C₂H₅ | H | H | H | —O— | —S— | —O— | $n_D^{20}$ 1,5808 |
| —C₂H₅ | CH₃ | H | H | —O— | —S— | —O— | $n_D^{20}$ 1,5709 |
| —CH₂—C≡CH | —CH₂—CH₂—CH₂—CH₂— | | H | —O— | —C(=O)— | —O— | |

| $R_1$ | $R_2$ | $R_3$ | $R_4$ | $R_5$ | W | Y | Z | Physical data |
|---|---|---|---|---|---|---|---|---|
| i-C₃H₇ | H | H | 4-Br | H | —O— | —S— | —O— | m.p.: 36–37°C |
| i-C₃H₇ | H | H | 4-CH₃ | H | —O— | —S— | —O— | $n_D^{20}$ 1,5718 |
| C₂H₅ | H | H | 4-CH₃ | H | —O— | —S— | —O— | $n_D^{20}$ 1,5808 |
| —CH₂—C≡CH | H | H | H | H | —S— | —CH₂— | —O— | |
| —CH₃ | —CH₃ | H | H | H | —O— | —CH₂— | —O— | |
| —CH₂—CH(CH₃)₂ | —CH₃ | H | H | H | —O— | —CH₂— | —O— | |
| —CH₃ | H | H | H | H | —O— | —CH₂— | —O— | |
| —CH₂—CH=CH₂ | H | H | H | H | —O— | —CH₂— | —O— | |
| —CH₃ | H | —CH₃ | H | H | —O— | —CH₂— | —O— | |
| —CH₂—C≡CH | —CH₂—CH₂—CH₂—CH₂— | | H | H | —O— | —CH₂— | —O— | |
| —CH₂—C≡CH | —CH₂—CH₂—CH₂—CH₂— | | H | H | —O— | —S— | —O— | |
| —CH—C≡CH<br>\|<br>CH₃ | H | H | H | H | —O— | —CH₂— | —O— | |

EXAMPLE 2

A. Contact Action on *Dysdercus fasciatus* Larvae

A specific amount of a 0.1% acetonic active-substance solution (corresponding to 10 mg of active substance per square meter) was transferred by pipet to an aluminum dish and uniformly distributed. After evaporation of the acetone, 10 larvae in the fifth stage of *Dysdercus fasciatus* were placed into the treated dish containing feed and moist cotton wool. The dish was then covered with a perforated lid. After about 10 days, i.e. as soon as the control insects had moulted into adults, the test insects were examined to determined the number of normal adults.

Compounds according to Example 1 exhibited a good action in the above test.

B. Contact Action on *Aedes aegypti* Larvae

About 20 2-day-old larvae of the yellow-fever mosquito (*Aedes aegypti*) were placed in position in a beaker containing a solution of the active substance (concentration 5 ppm). The beaker was then covered with a perforated lid. After the control insects had moulted into adults, the test insects were examined and the percentage of normal adults in comparison with the control adults was determined.

Compounds according to Example 1 exhibited a good action in the above test.

C. Contact Action on *Tenebrio molitor* Pupae

A specific amount of a 0.1% acetonic active-substance solution corresponding to 10 mg of active substance per square meter was transferred by pipet into an aluminum dish and uniformly distributed. After evaporation of the acetone, 10 freshly formed pupae were placed onto the treated surface, and the dish was covered with a perforated lid. After the control insects had left the cocoon as imagines, the test insects were examined to determine the number of normal adults.

Compounds according to Example 1 exhibited a good action in the above test.

EXAMPLE 3

A. Action Against *Musca domestica*

An amount in each case of 50 g of CSMA maggot substrate was weighed off in beakers. For each active substance, 2.5 ml of a 1% acetonic solution of the respective substance was transferred by pipet twice to 50 g of maggot substrate each time. After a thorough mixing of the treated substrate, the solvent was allowed to evaporate off. There were then deposited per active substance in each case 25 1-, 2- and 3-day-old maggots and about 50 fly eggs. After completion of pupation, the pupae were flushed out and counted. After a period of 10 days, the number of emerged flies was counted and hence any effect on metamorphosis was established.

Compounds according to Example 1 exhibited in this test a good action against *Musca domestica*.

B. Action Against *Ephestia kuhniella*

50 g of wheat flour was made up in two beakers with a specific amount of active substance to give a 5% dust, the concentration being 0.05%. Into each beaker (25 g of flour) there were placed 10 larvae of *Ephestia kuhniella*. The pattern of population was ascertained over a period of 8 weeks and the number of moths determined.

Compounds according to Example 1 exhibited a good action in this test against *Ephestia kuhniella*.

EXAMPLE 4

Action Against Red Spider Mites

*Phaseolus vulgaris* (bush beans) were infested, 12 hours before the test for acaricidal action, with an infested piece of leaf from a mass culture of *Tetranychus urticae*. The transferred mobile stages were sprayed with the emulsified test preparations, at a concentration of 0.04%, by means of a chromatography-sprayer in a manner ensuring no running-off of the spray liquor. An assessment was made after 2 to 7 days, by examination under a binocular, of the living and of the dead larvae, adults and eggs, and the results were expressed in percentages. The treated plants were kept during the holding time in greenhouse compartments at 25°C.

Compounds according to Example 1 exhibited in the above test a good action against eggs, larvae and adults of *Tetranychus urticae*.

We claim:
1. A compound of the formula

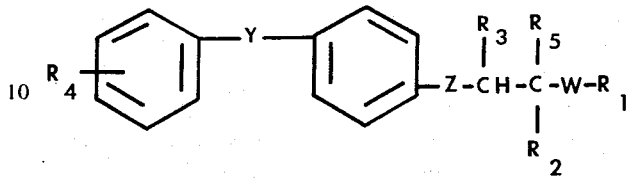

(1)

wherein
W and Z each represent —O—,
Y represents —CH$_2$—,
R$_1$ represents C$_1$–C$_6$-alkyl, C$_2$–C$_4$-alkenyl, C$_2$–C$_4$-haloalkenyl, C$_3$–C$_4$-alkenyl, C$_3$–C$_6$-cycloalkyl or benzyl,
R$_2$ represents hydrogen, methyl or ethyl,
R$_3$ represents hydrogen or methyl, or
R$_2$ and R$_3$ together with the chain represent a saturated 5- or 6-membered ring, and
R$_4$ represents hydrogen, methyl or halogen, and
R$_5$ represents hydrogen or methyl.

2. A compound according to claim 1 wherein
R$_1$ represents C$_1$–C$_6$-alkyl, C$_2$–C$_4$-alkenyl, C$_3$–C$_4$-chloroalkenyl or C$_3$–C$_4$-alkynyl,
R$_2$ represents hydrogen or methyl,
R$_3$ and R$_5$ represent hydrogen, and
R$_4$ represents bromine.

3. A compound according to claim 2 wherein
R$_1$ represents methyl, ethyl, isopropyl, isobutyl, sec.-butyl, allyl or propargyl, and
R$_2$ represents hydrogen or methyl, and
R$_3$, R$_4$ and R$_5$ each represent hydrogen.

4. Compound according to claim 3 of the formula

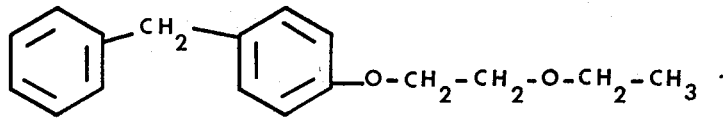

5. A compound according to claim 1 of the formula

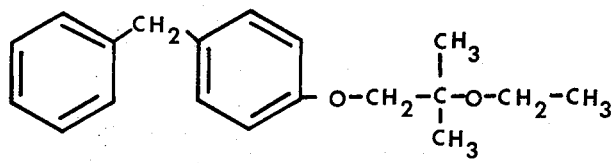

* * * * *

UNITED STATES PATENT OFFICE
CERTIFICATE OF CORRECTION

Patent No. 3,957,885  Dated May 18, 1976

Inventor(s) Friedrich Karrer et al.

It is certified that error appears in the above-identified patent and that said Letters Patent are hereby corrected as shown below:

Column 12, line 21 should read as follows:

haloalkenyl, $C_3$-$C_4$-alkynyl, $C_3$-$C_6$-cycloalkyl or

Signed and Sealed this

Seventeenth Day of August 1976

[SEAL]

Attest:

RUTH C. MASON
*Attesting Officer*

C. MARSHALL DANN
*Commissioner of Patents and Trademarks*